United States Patent [19]

Tigani

[11] 4,431,415
[45] Feb. 14, 1984

[54] DEVICE FOR REPLACING MISSING TEETH IN HUMAN DENTITION

[76] Inventor: Pasquale Tigani, 5219 Ridgefield Rd., Washington, D.C. 20016

[21] Appl. No.: 366,618

[22] Filed: Apr. 8, 1982

[51] Int. Cl.³ ............................................ A61C 13/22
[52] U.S. Cl. .................................................. 433/172
[58] Field of Search ............... 433/172, 177, 178, 191

[56] References Cited

U.S. PATENT DOCUMENTS 1,702,282  2/1929  Stoloff ................................ 433/172

Primary Examiner—Robert Peshock
Attorney, Agent, or Firm—Sughrue, Mion, Zinn, Macpeak and Seas

[57] ABSTRACT

The device which is adapted to be secured between two existing teeth is suitable for supporting an artificial denture to replace an anterior tooth or a posterior tooth. The device is comprised of a backing member having two complimentary parts which are mounted for sliding movement relative to each other. Each part is provided with a laterally extending projection adapted to be located in a groove in the side of an adjacent real tooth whereby upon sliding movement of the two parts, the distance between the ends of the projections can be shortened to allow placement of the device between two existing teeth. The two parts can then be slid relative to each other to extend the projections into the grooves in two spaced apart real teeth. A threaded clamping member is then tightened to secure the two parts against relative movement with respect to each other and a facing member is secured to the backing member.

4 Claims, 7 Drawing Figures

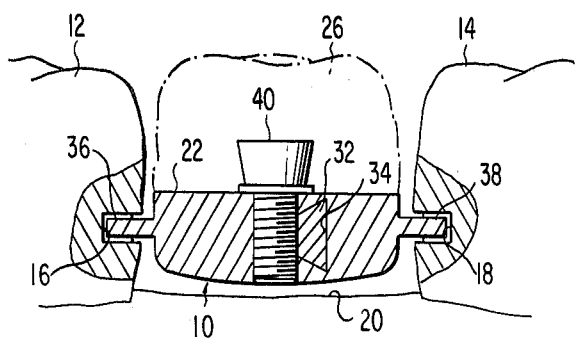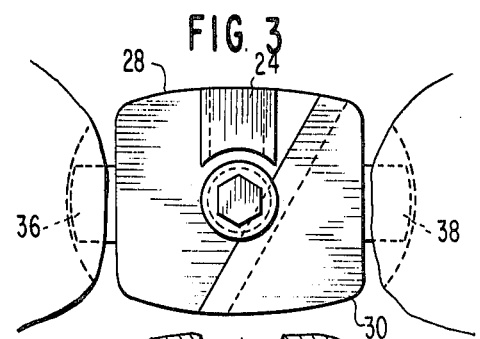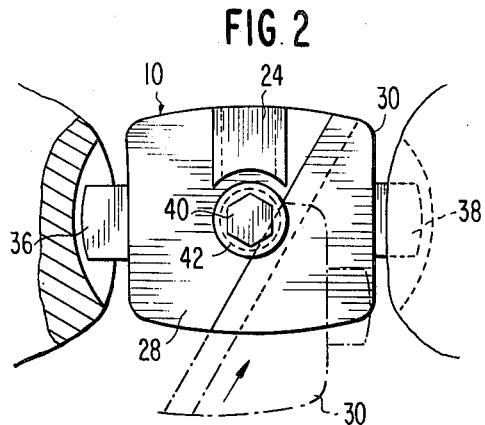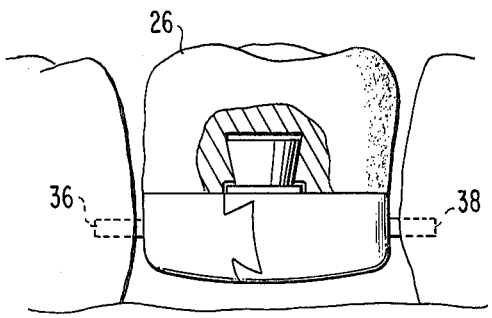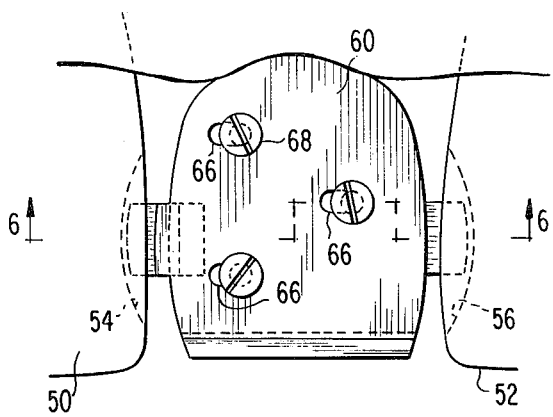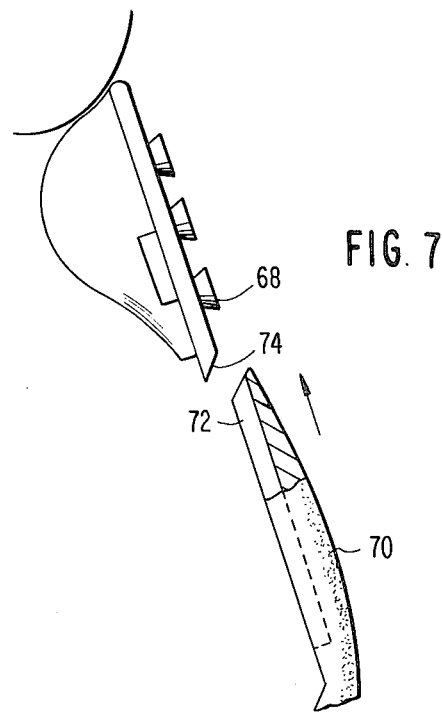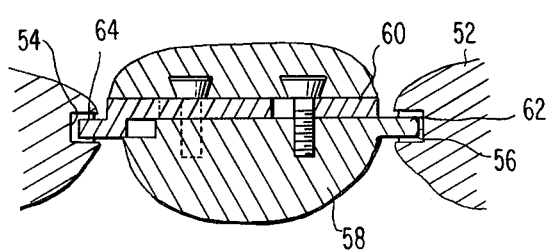

DEVICE FOR REPLACING MISSING TEETH IN HUMAN DENTITION

BACKGROUND OF THE INVENTION

The present invention is directed to an artifical denture and more specifically to the means for anchoring the artificial denture between two existing teeth.

It is old and well known in the artificial denture art to permanently secure a bridge in two opposed grooves in spaced apart existing teeth and to secure the artificial tooth or teeth to the bridge in a permanent or detachable manner. The grooves which must be cut in the natural teeth for anchoring the bridge therein are of a considerable magnitude and frequently have to be undercut in order to provide a complimentary interfitting engagement with enlarged projections on the opposite ends of the bridge. While the posterior teeth are usually of a sufficient size to permit the grinding of such large grooves, these methods are generally unsuitable for anterior teeth which are relatively thin.

Other artificial denture devices rely on anchoring a protruding post or bracket into spaced apart existing natural teeth and detachably or permanently securing the bridge to the protruding post or bracket. Once again, it is usually possible to anchor such a post or bracket in the relatively large posterior teeth but extremely difficult if not impossible to anchor such a post or bracket to the anterior teeth. While the use of telescopically adjustable bridge support elements is old and well known in the art, the telescopic adjustment must generally take place prior to the insertion of the bridge support device into the complimentary grooves in the spaced apart existing teeth. Thus, it is extremely difficult to obtain and maintain the proper telescopic relationship prior to the insertion of the device and during the subsequent removal of the bridge for fitting the facings on the bridge prior to the permanent anchoring of the bridge in the existing teeth.

The U.S. Patent to Plotnick No. 2,835,034 discloses a removable denture having a housing secured to a base or saddle adapted to rest on the gum. An artificial tooth or crown is arranged to fit over the housing and is secured to a vertically movable plunger mounted for sliding movement in the housing. The base member is designed to protrude under the overhanging portion of an adjacent tooth on one side and to prevent the vertical movement of the artificial tooth a laterally extending plunger is slidably located in the housing for movement into engagement with the undercut portion of an adjacent tooth on the opposite side. The two plungers are provided with beveled edges which bear against each other within the housing so that as the artificial tooth or crown is moved downwardly over the housing 16, the laterally movable plunger will be cammed outwardly by the vertically moving plunger into engagement with the adjacent tooth, thereby preventing vertical movement of the entire artificial tooth assembly. The cam surfaces on the ends of the plunger disengage when the artificial tooth or crown is moved into final position on the housing thereby eliminating any camming action between the plungers during normal use.

Applicant's own U.S. Pat. No. 4,163,318 is directed to a device for replacing missing teeth in human dentition. The device which is adapted to be secured between two existing teeth is suitable for supporting an artificial denture to replace an anterior tooth or a posterior tooth. The device is comprised of a backing member having a pair of parallel extendable arms slidably disposed in grooves in said backing member on opposite sides of a pinion rotatably mounted in said backing member in simultaneous meshing engagement with teeth on both arms for simultaneously extending both arms in opposite directions upon rotation of said pinion in one direction. The extended ends of each arm is adapted to be disposed in a precut groove in an existing tooth to support the device between two existing teeth. Suitable projections are provided on the surface of the backing member for cooperation with complimentary grooves in the artificial facing. The facing is secured to the backing and the extended arms are secured in the grooves of adjacent teeth by a suitable cement or filling material.

SUMMARY OF THE INVENTION

The present invention provides a backing device for an artificial denture having readily expansible and contractable anchoring means which can be moved into and out of opposing grooves in spaced apart existing teeth with a minimum of effort and which will maintain their adjusted position until such time as the anchoring means can be permanently secured to the existing teeth.

The present invention provides a backing device for artificial dentures which is adapted to be secured to spaced apart existing teeth in a manner which requires minimal cutting of the existing teeth so as not to structurally weaken the existing teeth or to provide unduly deep cuts which would lead to the early decay and destruction of the existing teeth.

The present invention provides a backing device for artificial dentures having readily adjustable anchoring means suitable for engagement with thin anterior teeth as well as posterior teeth.

The present invention provides a device suitable for replacing missing teeth in human dentition comprising a two-part backing member adapted to be disposed between two spaced apart existing teeth. The two parts define a substantially rectangular member disposed in a horizontal plane when assembled together along a substantially diagonal interface. The two diagonal complimentary faces of each part are provided with a tongue and groove connection so as to permit the two parts to slide relative to each other in a horizontal plane. Each part is provided with an anchoring projection adapted to extend into a complimentary groove in an adjacent tooth. Screw means are provided for securing the two parts against relative movement to securely locate the oppositely directed projections in the grooves of adjacent teeth. A facing is secured to the backing member by a suitable interfitting connection and/or adhesive means which will also prevent movement of the two parts of the backing member relative to each other. For anterior teeth the two parts of the backing member are provided with complimentary vertical mating faces with each part having a lateral projection for engagement in a groove of an adjacent tooth. A plurality of clamping screws are threaded into one part of the backing member through elongated adjusting slots in the other member whereby upon location of the backing member between two teeth with the projections located in corresponding grooves in said teeth, the clamping screws may be tightened to retain the backing member between said teeth. The facing is secured to one of the backing parts by suitable interfitting means and/or an adhesive to further secure the two parts against relative movement to each other. In both embodiments, the edges of the backing member facing outwardly of the mouth may be beveled and the facing member may be provided with a corresponding overhang to aid in completely hiding the backing member from view.

The foregoing and other objects, features and advantages of the invention will be apparent from the following more particular description of preferred embodiments of the invention as illustrated in the accompanying drawings.

BRIEF DESCRIPTION OF THE DRAWINGS

FIG. 1 is a vertical cross-sectional view of the backing device according to the present invention secured between two existing teeth with the facing shown in dotted lines.

FIG. 2 is a top plan view of the device of FIG. 1 with one part of the backing member shown in solid lines and dotted lines in two different positions.

FIG. 3 is a top plan view of the backing device according to the present invention secured between two existing teeth with the facing shown in exploded relationship thereto prior to assembly.

FIG. 4 is a side elevation view, partly broken away of the backing device according to the present invention with the facing secured thereto.

FIG. 5 is a vertical elevational view of a modified form of backing device according to the present invention secured between two existing teeth with the facing removed.

FIG. 6 is a sectional view taken along the line V—V of FIG. 5.

FIG. 7 is a side elevation view, partly broken away showing the device of FIG. 5 with the facing about to be assembled therewith.

DETAILED DESCRIPTION OF THE INVENTION

The artificial denture arrangement according to the present invention is suitable for a connection between two spaced apart existing teeth which may be posterior teeth, anterior teeth or one of each. The present invention is disclosed in the present application only with respect to situations where a single tooth is missing but it is obvious that the size of the device could be varied to provide support for a plurality of artificial teeth.

The backing support member 10 as shown in FIG. 1 is disposed between two spaced apart existing posterior teeth 12 and 14. A pair of small opposed grooves 16 and 18 are cut into the teeth 12 and 14 respectively, transversely to the direction of growth of the teeth. The backing member 10 which is constructed of chrome cobalt metal, stainless steel or any other suitable material has a substantially rectangular configuration as best seen in FIG. 2 while the underside of the member 10 is merely rounded off as best seen in FIG. 1 so as to be disposed in close proximity to the gum 20. The backing member 10 is provided with a flat upper surface 22 having one or more projections 24 extending upwardly therefrom and adapted tobe disposed in mating relation with a complimentary groove in the standard facing 26 which may be of any suitable material such as porcelain, gold or the like. The facing 26 may be secured to the backing member by any suitable dental cement. The backing member 10 is comprised of two mating parts 28 and 30 which mate along a substantially diagonal line as best seen in FIGS. 2 and 3. The mating faces of the two parts 28 and 30 are formed with a complimentary tongue 32 and groove 34, respectively, so that the two parts 28 and 30 are slidable relative to each other. The two parts 28 and 30 are each provided with a laterally extending projections 36 and 38, respectively, which are of integral one-piece construction with each half.

In order to locate the backing member between two existing teeth such as the teeth 12 and 14 the portion 30 of the backing member is moved to the dotted line position relative to the member 28 as seen in FIG. 2. When the two parts 28 and 30 are in this position, the distance between the ends of the projections 36 and 38 is shortened thereby allowing the backing member 10 to be placed between the two teeth 12 and 14 with the projection 36 located in the groove 16 in the tooth 12. The part 30 is then moved to the solid line position as shown in FIG. 2 to locate the projection 38 firmly within the groove 18 in the tooth 14. A bolt or screw member 40 having a flange 42 is threaded into an aperture in the part 28 which is located close to the tongue 32 so that upon tightening of the screw or bolt 40 the flange 42 will overlap and clamp the part 30 against relative movement with respect to the part 28. The facing 26 is then secured to the backing member 10 by means of the dove-tailed shaped projection 24 on the backing member 28 engaging the complimentary groove 44 in the facing 26. An adhesive is used to secure the projection 24 within the groove 44 and to secure the planar surface of the facing to the upper surface 22 of the two parts 28 and 30 of the backing member to further secure the two parts against relative movement with respect to each other. While the facing member is shown as only covering the upper flat surface 22 of the backing member 10 it is also possible to have the front side of the facing 26 opposite the groove 44 overlap the front surface of the backing member 20 to completely hide the backing member from view. This is not as critical with posterior teeth as with anterior teeth as will be described hereinafter.

The head of the screw or bolt 40 may also be provided with undercut sides as best seen in FIGS. 1 and 4 which will also mate with the groove 44 in the facing 26 to help retain the facing on the backing member. If the facing overlaps the base member 10 on one or more sides, the projection 24 could be eliminated since the overlap would prevent any relative rotation of the facing 26 on the base member 10.

While the foregoing embodiment was described with respect to a replacement denture for posterior teeth, the embodiment of FIGS. 5–7 shows a suitable replacement denture device for use between two anterior teeth. Since the anterior teeth 50 and 52 are relatively thin, the grooves 56 and 54 for anchoring the base member of the replacement denture are cut into the teeth in the direction of growth of the teeth. The backing member 58 is comprised of a back part 58 and a front part 60 which are slidably disposed relative to each other. The back part 58 and the front part 60 are each provided with a laterally extending projection 62 and 64, respectively, which are adapted to extend into the grooves 56 and 54. The front part 60 is provided with a plurality of elongated slots 66 arranged in a substantially triangular pattern as seen in FIG. 5. Three screws or bolts 68 extend through the slots 66 into threaded engagement with apertures in the back member 58. In order to insert the backing member between the two anterior teeth 50 and 52, the screws or bolts 68 are loosened thereby allowing the front member 60 to slide relative to the rear member 58 in order to shorten the distance between the tips of the two projections 62 and 64 in order to allow the backing member to be placed between the two teeth. The front and rear members are then slid relative to each other to bring the projections 62 and 64 into the grooves 56 and 54. The screws or bolts 68 are then tightened to prevent further relative movement of the two parts 58 and 60 relative to each other. A facing member 70 having a plurality of grooves 72 is then secured to the front part 60. Grooves 72 have a cross-section complimentary to the tapered sides of the heads on the screws or bolts 68 to assist in anchoring the facing to the backing member. The triangular configuration of the screws or bolts 68 prevents rotational movement facing relative to the backing member. A suitable adhesive is used to assist in securing the facing to the backing member and to secure the two parts of the backing member against relative movement with respect to each other. The backing member may be provided with a beveled edge 74 so as to allow the facing 70 to taper down to a relatively sharp edge of the type found on anterior teeth with still enabling the facing to completely cover the edge of the backing member.

While the invention has been particularly shown and described with reference to preferred embodiments thereof it will be understood by those in the art that the foregoing and other changes in form and details may be made therein without departing from the spirit and scope of the invention.

I claim:

1. An artificial denture device comprising a backing member comprised of two complementary parts, means for connecting said two parts to each other against lateral separation while permitting sliding movement relative to each other, each of said parts having a projection extending in opposite directions relative to each other and securing means for securing said two parts to each other to prevent sliding movement, said two parts defining a flat upper surface having a substantially rectilinear outline, while being separated along a substantially diagonal line to define two mating surfaces, tongue and groove means formed on said mating surface to allow sliding movement of one part relative to the other along said diagonal line and said securing means being comprised of a threaded member having an enlarged head, a corresponding threaded aperture in one of said members adjacent to the diagonal line whereby said enlarged head overlaps said diagonal line to secure said two parts against movement relative to each other upon tightening of said threaded member in said threaded aperture.

2. An artificial denture as set forth in claim 1, further comprising facing means adapted to be secured to said backing member to cover said securing means, said head of said threaded member being provided with undercut side surfaces and said facing means being provided with a groove having a complementary configuration to assist in retaining said facing member on said backing member.

3. An articificial denture device comprising a backing member comprised of two complementary parts, means for connecting said two parts to each other against lateral separation while permitting sliding movement relative to each other, each of said parts having a projection extending in opposite directions relative to each other, securing means for securing said two parts to each other to prevent sliding movement and facing means adapted to be secured to said backing member to cover sai securing means wherein said two parts are provided with flat complementary surfaces substantially co-extensive with each other, elongated slot means formed in one of said members, threaded aperture means formed in the other of said parts in alignment with said elongated slot means and at least one threaded member having a head adapted to clamp said two parts against movement relative to each other, said head being provided with undercut tapered sides and said casing means being provided with grooves complementary to said tapered sides to assist in retaining said facing means on said backing member and wherein said projections extend laterally of said members in a common plane parallel to the flat complementary surfaces of said parts.

4. An artificial denture as set forth in claim 3 wherein a plurality of said threaded members are provided for securing said parts together and said facing means are provided with a plurality of complementary grooves for the heads on said threaded members to prevent rotation of said facing means in a plane parallel to said complementary flat faces.

* * * * *